United States Patent [19]
Franz

[11] 3,993,467
[45] Nov. 23, 1976

[54] HYDROXYALKYL ESTERS OF N-PHOSPHONOMETHYL GLYCINE AND THE HERBICIDAL USE THEREOF
[75] Inventor: John E. Franz, Crestwood, Mo.
[73] Assignee: Monsanto Company, St. Louis, Mo.
[22] Filed: Nov. 13, 1975
[21] Appl. No.: 631,764

Related U.S. Application Data
[62] Division of Ser. No. 495,011, Aug. 5, 1974, Pat. No. 3,948,975.

[52] U.S. Cl. .................................. 71/86; 260/482 R
[51] Int. Cl.$^2$ .......................................... A01N 9/36
[58] Field of Search .................................... 71/86

[56] References Cited
UNITED STATES PATENTS

| | | | |
|---|---|---|---|
| 3,453,301 | 7/1969 | Uhing | 71/86 X |
| 3,455,675 | 7/1969 | Irani | 71/86 |
| 3,799,758 | 3/1974 | Franz | 71/86 |
| 3,853,530 | 12/1974 | Franz | 71/86 X |
| 3,929,450 | 12/1975 | Hamm et al. | 71/86 |

*Primary Examiner*—Joseph Paul Brust
*Attorney, Agent, or Firm*—William T. Black; Donald W. Peterson

[57] ABSTRACT

Hydroxyalkyl esters of N-phosphonomethyl glycine and their salts and a process for their preparation are described. These esters and salts are useful as contact herbicides.

10 Claims, No Drawings

HYDROXYALKYL ESTERS OF N-PHOSPHONOMETHYL GLYCINE AND THE HERBICIDAL USE THEREOF

This is a division of application Ser. No. 495,011 filed Aug. 5, 1974, now U.S. Pat. No. 3,948,975.

This invention relates to novel hydroxyalkyl esters of N-phosphonomethyl glycine and to salts thereof, to herbicidal compositions containing same and to herbicidal methods employing such compounds and compositions.

N-phosphonomethyl glycine and its salts are contact herbicides which have little or no residual soil activity. This is shown in U.S. Pat. No. 3,799,758.

The novel hydroxyalkyl esters of the present invention have the formula

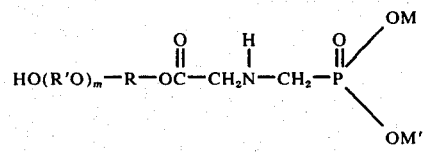

wherein R is an alkylene or alkoxy substituted alkylene containing up to 18 carbon atoms, R' is alkylene or alkoxy substituted alkylene groups containing from 2 to 4 carbon atoms, m is an integer of from 0 to 3 and M is hydrogen and M' is hydrogen, alkali metal, alkaline earth metal, ammonium or organic ammonium.

The hydroxyalkyl esters of this invention are prepared by standard esterification procedures. For example, N-phosphonomethyl glycine is mixed with an excess of a dihydric alcohol in the presence of an acid such as hydrogen chloride and the mixture heated. The water produced by the esterification reaction can be removed by distillation with the excess dihydric alcohol or an azeotroping agent such as toluene can be added and the water removed by azeotroping. Any excess dihydric alcohol can be removed by vacuum distillation to leave the hydroxyalkyl ester of N-phosphonomethyl glycine as the residue.

It is, of course, apparent to those skilled in the art that for best yields the molar ratio of N-phosphonomethyl glycine to dihydric alcohol should be less than 1 to 1 and preferably at least 1 to 2 or even greater to insure only one hydroxyl group of the dihydric alcohol is esterified.

The reaction is conducted in the presence of an acid catalyst. Any strong acid normally employed for esterification reaction can be employed. Thus, for example, one can employ sulfuric acid, benzene sulfonic acid, the halogen acids such as HCl, HBr, HI and strong acids such as trifluoroacetic acid, pentafluoropropionic acid, heptafluorobutyric acid and the like. For convenience and ease of removal of the acid catalyst, it is preferred to employ the volatile acids such as hydrochloric, trifluoroacetic and the like.

The reaction is normally conducted at atmospheric pressure for convenience. Super atmospheric and sub-atmospheric pressures can also be employed if desirable. Sub-atmospheric pressures are suitable for removal of water and excess reactants and solvents.

The temperature at which the reaction is conducted can vary from as low as 20° C. to 150° C. or even higher. It is preferred to conduct the reaction at temperatures of from 25° C. to about 100° C.

The term "alkali-metal" as employed herein encompasses lithium, sodium, potassium, cesium and rubidium; and the term "alkaline earth metal" includes beryllium, magnesium, calcium, strontium and barium.

The organic ammonium salts included in the above formula are those prepared from low molecular weight organic amines, i.e., having a molecular weight below about 300, and such organic amines include the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine.

The groups $HO(R'-O-)_m-R-$ in the above formula represent, for example, hydroxyalkyl groups containing from 2 to 18 carbon atoms, hydroxy(polyalkylene oxy groups) such as, hydroxyalkoxyalkyl, hydroxyalkoxyalkoxyalkyl, hydroxyalkoxyalkoxyalkoxyalkyl, hydroxyalkoxy(alkoxy)alkyl, hydroxyalkoxyalkoxy(alkoxy)alkyl and the like in which each group in the linear chain contains from 2 to 4 carbon atoms and any alkoxy side chains contain 1 to 4 carbon atoms.

Examples of the starting dihydroxy alcohols from which the hydroxyalkyl N-phosphonomethyl glycinates of this invention are prepared are ethylene glycol, 1,2- and 1,3-propylene glycols, the 1,2-, 1,3-, 1,4-, and 2,3-butylene glycols, the pentylene glycols, the hexylene glycols, the decane diols, diethylene glycol, triethylene glycol, dipropylene glycol, tripropylene glycol, 3-methoxy-1,2-propane diol, 2-methoxy-1,3-propane diol, hydroxyethoxyethoxyethanol, 3-hydroxypropoxyethoxyethanol, 3-hydroxypropoxypropanol, 4-hydroxybutoxybutoxybutanol-1 and those polyoxyalkylene glycols having 2 or more different alkylene groups in the chain.

It is, of course, apparent to those skilled in the art that when the polyoxyalkylene dihydric alcohols containing more than one type of alkylene group in the molecule are employed, that mixed hydroxyalkyl esters will be obtained.

The following examples serve to further illustrate the invention. In the examples, all parts and percents are by weight unless otherwise expressly set forth.

EXAMPLE 1

Into a 200 ml. round bottom flask was charged N-phosphonomethyl glycine (9.0 grams) and ethylene glycol (about 60 ml.). The mixture was stirred and hydrogen chloride gas was bubbled into the reaction mixture which became homogenous in approximately ½ hour with an exotherm to 65° C. Hydrogen chloride gas was continued to be passed into the reaction mixture while the temperature returned to room temperature (approximately 2½ hours). The excess ethylene glycol was distilled off under reduced pressure of 0.40 mm Hg leaving a white gummy residue. The gummy residue was triturated with ethanol to yield 7.9 grams of a fine white powder having a melting point of 192°–193.5° C with decomposition. The white powder was identified as 2-hydroxyethyl-N-phosphonomethyl glycinate. (Compound I).

Anal. Calc'd for $C_5H_{12}NO_6P$: C 28.18; H 5.68; N 6.57 Found: C 28.39; H 5.75; N 6.39

EXAMPLE 2

Into a 100 ml. three-neck flask was charged 4 grams of N-phosphonomethyl glycine and 45 grams of 1,3-propanediol. The mixture was stirred while hydrogen chloride gas was bubbled through. The temperature rose to 50° C and in 30 minutes the reaction became homogenous. Hydrogen chloride continued to be bubbled into this mixture for 1¾ hours while the reaction temperature dropped to approximately 25° C. The excess propanediol was distilled off under vacuum of 1–2 mm. mercury. When substantially all of the excess propanediol was removed, the product crystallized out. This solid product was triturated with ethanol several times to yield 4.45 grams of a fine white solid having a melting point of 189°–189.5° C with decomposition which was identified as 3-hydroxypropyl-N-phosphonomethyl glycinate. (Compound II).

Anal. Calc'd for $C_6H_{14}NO_6P$: C 31.72; H 6.21; N 6.17 Found: C 31.75; H 6.25; N 6.17

EXAMPLE 3

Into a three-neck 100 ml. round bottom flask was charged N-phosphonomethyl glycine (4.0 grams) and butanediol (52.7 grams). The mixture was stirred and hydrogen chloride gas bubbled through the reaction mixture. The temperature rose to 90° C while the reaction mixture slowly became homogenous. The HCl addition was continued for 2 hours as the temperature dropped to 30° C. The excess 1,4-butanediol was distilled off leaving a solid residue. The solid residue was triturated with ethanol, then ether to give a fine white solid (4.75 grams) having a melting point of 177°–177.5° C with decomposition. This white solid was identified as 98.5% pure 4-hydroxybutyl-N-phosphonomethyl glycinate. (Compound III).

Anal. Calc'd for $C_7H_{16}NO_6P$: C 34.86; H 6.69; N 5.81 Found: C 34.39; H 6.51; N 5.55

EXAMPLE 4

Into a 100 ml. four-neck flask was charged N-phosphonomethyl glycine (4.0 grams) and diethylene glycol (43.5 grams) and the mixture stirred. Hydrogen chloride gas was bubbled through the reaction mixture with stirring while the reaction mixture became homogenous in about 15 minutes with an exotherm to 62° C. The hydrogen chloride gas was continued to be bubbled through the solution over a 3 hour period while the temperature decreased to 30° C. The excess diethyleneglycol was distilled off under reduced pressure leaving a gummy residue. The gummy residue was triturated with ethanol to obtain a solid (5.05 grams). This solid had a melting point of 153.5°–155° C with decomposition and was identified as 2-hydroxyethoxyethyl-N-phosphonomethyl glycinate. (Compound IV).

Anal. Calc'd for $C_7H_{16}NO_7P$: C 32.69; H 6.27; N 5.45 Found: C 32.75; H 6.25; N 5.34

EXAMPLE 5

Into a 100 ml. round bottom flask was charged 3.1 grams of N-phosphonomethyl glycine and 40.3 grams of molten 1,6-hexanediol. The mixture was maintained at 100° C and HCl gas passed in until a solution was obtained (½ hour). Introduction of HCl was continued for 1½ hours at 90° C and then excess alcohol was removed by distillation at reduced pressure. The residue was triturated with ethanol and then ether to yield 3 grams of 6-hydroxyhexylphosphonomethyl glycinate decihydrochloride, M.P. 166.5°–172° C (dec.). (Cpd. V)

Anal. Calc'd for $C_9H_{20}NO_6P$. 0.1 Hcl: C 39.63; H 7.43; N 5.14; Cl 1.26 Found: C 39.42; H 7.40; N 5.03; Cl 1.26

EXAMPLE 6

Into a 100 ml. round bottom flask is placed 21.3 grams (0.10 mole) of 2-hydroxyethyl-N-phosphonomethyl glycinate and 50 mls of water. The mixture is stirred rapidly as 4 grams (0.10 mole) of sodium hydroxide is added slowly while maintaining the temperature below 30° C by means of a water bath. The clear solution thus obtained contains the monosodium salt of 2-hydroxyethyl-N-phosphonomethyl glycinate which may be obtained as a white powder on concentration of the solution at reduced pressure.

By following the procedure of Example 6 and employing the proper base or ammonium compound, the following salts can be prepared:

Monobutylamine salt of 2-hydroxyethyl-N-phosphonomethylglycinate

Mono-(trimethylamine) salt of 2-hydroxyethyl-N-phosphonomethylglycinate

Mono(diethylenetriamine) salt of 2-hydroxyethyl-N-phosphonomethylglycinate

Monoisopropylamine salt of 3-hydroxypropyl-N-phosphonomethylglycinate Mono-n-propylamine salt of 4-hydroxybutyl-N-phosphonomethylglycinate Mono(dipropargylamine) salt of 2-hydroxyethoxyethyl-N-phosphonomethylglycinate Monosodium salt of 2-hydroxyethoxypropyl-N-phosphonomethylglycinate Potassium salt of 2-hydroxypropoxypropyl-N-phosphonomethylglycinate Mono(diallylamine) salt of 2-hydroxyethyl-N-phosphonomethylglycinate

EXAMPLE 7

The post-emergent herbicidal activity of the compounds of this invention is demonstrated as follows. The active ingredients are applied in spray form to 14 or 21 day old specimens of the various plant species. The spray, a water solution containing the active ingredient and a surfactant (35 parts butylamine salt of dodecylbenzene sulfonic acid and 65 parts tall oil condensed with ethylene oxide in the ratio of 11 moles ethylene oxide to 1 mole tall oil) is applied to the plants in different sets of pans at several rates (pounds of active ingredient per acre). The treated plants are placed in a greenhouse and the effects are observed and recorded after approximately 2 weeks or approximately 4 weeks as is indicated in the table.

The post-emergence herbicidal index used in the table is as follows:

| PLANT RESPONSE | INDEX |
|---|---|
| No Injury | 0 |
| Slight Injury | 1 |
| Moderate Injury | 2 |
| Severe Injury | 3 |
| Killed | 4 |

TABLE I

| Cpd. | Rate lb/acre | Observation Time | Canada Thistle | Cocklebur | Velvet leaf | Morning-glory | Lambs-quarters | Smart-weed | Nuts-edge | Quack-grass | Johnson grass | Donny Brome | Barnyard Grass |
|---|---|---|---|---|---|---|---|---|---|---|---|---|---|
| I | 4 | A | 4 | 4 | 4 | 2 | 3 | 2 | 1 | 1 | 2 | 2 | 2 |
| II | 4 | A | 4 | 4 | 3 | 3 | 4 | 4 | — | 4 | 4 | 3 | 4 |
|  |  | B | 4 | 4 | 4 | 4 | 4 | 4 | — | 4 | 4 | 4 | 4 |
| III | 4 | A | 4 | 3 | 2 | 2 | 1 | 1 | 0 | 1 | 4 | 0 | 2 |
|  |  | B | 4 | 4 | 2 | 3 | 1 | 2 | 2 | 3 | 4 | 3 | 3 |
| IV | 4 | A | 4 | 3 | 3 | 2 | 2 | 2 | 2 | 3 | 2 | 2 | 2 |
|  |  | B | 4 | 4 | 4 | 2 | 4 | 4 | 3 | 4 | 3 | 2 | 4 |
| V | 4 | A | 2 | 2 | 1 | 2 | 4 | 2 | 1 | 3 | 1 | 1 | 3 |
|  |  | B | 2 | 3 | 3 | 3 | 4 | 4 | 3 | 4 | 3 | 2 | 4 |

A - Observed 2 weeks after treatment
B - Observed 4 weeks after treatment

For the sake of brevity and simplicity, the term "active ingredient" is employed hereinafter in this specification to describe the hydroxyalkyl ester of N-phosphonomethyl glycine derivatives of this invention, hereinbefore described.

In herbicidal compositions, the active ingredient can be admixed with one or more adjuvants which can be solid or liquid extenders, carriers, diluents, conditioning agents and the like. The herbicidal formulations comprise wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in U.S. Patents, bulletins and textbooks.

The preparation, formulations and particle size of the wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable or soluble powder, or wettable dust formulations; 5 to 95 parts by weight per 100 parts by weight emulsifiable oil formulations. The water formulations usually contain from 1 to 20 parts by weight of the active ingredient which can be further diluted for application. Formulations containing other than the above quantities of active ingredient can easily be prepared by those skilled in the art.

Application of the herbicidal compositions of this invention to the plant is well known to those skilled in the art. The application of liquid and particulate solid herbicidal formulations to the above-ground portions of plants can be carried out by conventional methods, e.g., power dusters, boom and hand sprayers and spray dusters, however, since most of the compositions of this invention are water soluble, it is preferred to apply them in an aqueous medium.

The active ingredient can be admixed with 1 or more adjuvants which can be solid or liquid extenders, carriers, diluents, conditioning agents and the like to form herbicidal compositions. Herbicidal formulations contain the active ingredients of this invention with wettable powders, aqueous suspensions, dust formulations, emulsifiable oils and solutions in solvents. In general, these formulations can all contain one or more surface-active agents. Herbicidal mixtures are applied at a rate of from 0.1 to 50 kg of active ingredient per hectare for general herbicidal effect.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

What is claimed is:

1. A herbicidal composition comprising a herbicidally effective amount of a compound of the formula

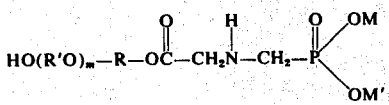

wherein R is an alkylene or alkoxy substituted alkylene containing up to 18 carbon atoms, R' is alkylene or alkoxy substituted alkylene groups containing from 2 to 4 carbon atoms, m is an integer of from 0 to 3 and M is hydrogen and M' is hydrogen, alkali metal, alkaline earth metal, ammonium or organic ammonium together with an inert carrier.

2. A herbicidal composition of claim 1 wherein m is 0 and said R group contains 2 to 12 carbon atoms.

3. A herbicidal composition of claim 2 wherein M and M' are hydrogen.

4. A herbicidal composition of claim 1 wherein m is 1, R and R' contain from 2 to 4 carbon atoms and M and M' are hydrogen.

5. A herbicidal composition of claim 1 wherein the compound is 3-hydroxy propyl-N-phosphonomethyl glycinate.

6. A herbicidal method which comprises contacting a plant with a herbicidally effective amount of a compound of the formula

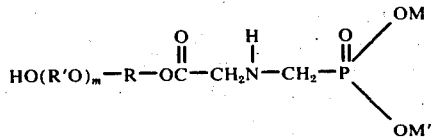

wherein R is an alkylene or alkoxy substituted alkylene containing up to 18 carbon atoms, R' is alkylene or alkoxy substituted alkylene groups containing from 2 to 4 carbon atoms, $m$ is an integer of from 0 to 3 and M is hydrogen and M' is hydrogen, alkali metal, alkaline earth metal, ammonium or organic ammonium.

7. A herbicidal method of claim 6 wherein $m$ is 0 and said R group contains 2 to 12 carbon atoms.

8. A herbicidal method of claim 7 wherein M and M' are hydrogen.

9. A herbicidal method of claim 6 wherein $m$ is 1, R and R' contain from 2 to 4 carbon atoms and M and M' are hydrogen.

10. A herbicidal method of claim 6 wherein the compound is 3-hydroxypropyl-N-phosphonomethyl glycinate.

* * * * *